United States Patent [19]

Yokoyama et al.

[11] Patent Number: 5,476,787
[45] Date of Patent: Dec. 19, 1995

[54] METHOD OF REMOVING NITROGEN IMPURITIES FROM WATER USING HYDROCARBON-PRODUCING MICROALGA

[75] Inventors: Shinya Yokoyama; Shigeki Sawayama; Tomoaki Minowa; Yutaka Dote, all of Tsukuba, Japan

[73] Assignee: Director-General of Agency of Industrial Science and Technology, Japan

[21] Appl. No.: 191,457

[22] Filed: Feb. 3, 1994

Related U.S. Application Data

[63] Continuation-in-part of Ser. No. 24,362, Mar. 1, 1993, abandoned.

[30] Foreign Application Priority Data

Apr. 24, 1992 [JP] Japan .................................. 4-132043

[51] Int. Cl.⁶ ............................. C02F 3/00; C02F 3/30; C12P 5/00; C12N 1/12
[52] U.S. Cl. ..................... 435/262.5; 210/601; 210/605; 435/166; 435/257.1; 435/262; 435/946
[58] Field of Search ................................. 435/262, 262.5, 435/257.1, 166, 946; 210/601, 605

[56] References Cited

U.S. PATENT DOCUMENTS

| | | | |
|---|---|---|---|
| 3,862,112 | 1/1975 | Ishida et al. | 260/112 R |
| 3,885,050 | 5/1975 | Ridgway, Jr. et al. | 426/60 |
| 3,891,772 | 6/1975 | Ridgway, Jr. et al. | 426/60 |
| 4,115,949 | 9/1978 | Avron et al. | 47/1.4 |
| 4,721,585 | 1/1988 | Santolini et al. | 210/616 |
| 5,011,604 | 4/1991 | Wilde et al. | 210/602 |

FOREIGN PATENT DOCUMENTS

| | | |
|---|---|---|
| 2461003 | 1/1981 | France . |
| 6060699 | 5/1981 | Japan . |
| 5301097 | 11/1993 | Japan . |

OTHER PUBLICATIONS

Mitsuda, "Protein isolates from Chlorella algae, Torula yeasts, & hydrocarbon–assimilating microorganisms", J. Nutr. Sci, 1973, (pp. 1–13) abst.

Japanese Abstract JP56060699A, "Dehydration of sludge from treatment . . . ", 1981, Abstract.

Chu et al., "Enzyme–linked immunosorbent . . . ", 1990, see abstract.

*Primary Examiner*—David M. Naff
*Assistant Examiner*—Deborah K. Ware
*Attorney, Agent, or Firm*—Lorusso & Loud

[57] ABSTRACT

Water containing an inorganic nitrogen-containing compound, such as water effluent from sewage treatment plant, is treated for the removal of the nitrogen-containing compound and for the production of hydrocarbons by proliferating microalga capable of consuming the nitrogen-containing compound and of producing the hydrocarbons as an intracellular product. After adjusting the water content, the resulting culture containing the proliferated microalga and clean water is heated at a high temperature and a high pressure to liberate the hydrocarbon from the microalga. The hydrocarbon is subsequently recovered by solvent extraction. Preferably the method of treating water for nitrogen impurities is carried out by culturing a proliferating hydrocarbon-producing microalga in contaminated water to obtain the proliferated microalga and purified water, then removing part of the purified water to obtain a first mixture containing the proliferated microalga and 60–98% by weight of water; further dissolving an alkaline substance in the first mixture to obtain a second mixture, applying heat to the second mixture in order to lyse and free the hydrocarbons from the microalga to form a third mixture. From the third mixture a free hydrocarbon product may be obtained.

11 Claims, 3 Drawing Sheets

METHOD OF REMOVING NITROGEN IMPURITIES FROM WATER USING HYDROCARBON-PRODUCING MICROALGA

CROSS-REFERENCE TO RELATED APPLICATION

This application is a continuation-in-part of U.S. Ser. No. 08/024,362 filed Mar. 1, 1993 now abandoned.

BACKGROUND OF THE INVENTION

This invention relates to a method of treating inorganic nitrogen compound-containing water such as water effluent from a sewage treatment plant and, more particularly, to a method of treating such nitrogen compound-containing water using microalgae.

A method has been proposed for the treatment of water effluent from sewage treatment facilities, wherein inorganic phosphorus compounds contained in the water effluent are consumed as nutrients by alga, such as Phormidium, Scenedesmus or Philodina, so that the disposed water can be purified as the algae proliferate. The known method, however, has a problem in disposition of the proliferated alga.

SUMMARY OF THE INVENTION

The present invention provides a method of treating water containing one or more inorganic nitrogen compounds for the reduction of the content of the inorganic nitrogen compounds while producing a useful product. The method includes a step of cultivating or proliferating microalgae capable of consuming the nitrogen-containing compounds and of producing one or more hydrocarbons as an intracellular product. By this, the nitrogen-containing compounds are consumed by the microalgae while the hydrocarbons are accumulated in the proliferated microalgae.

In one embodiment, the resulting cultivated mixture is separated into a solid phase containing the proliferated microalgae and a liquid phase having a lower concentration of the inorganic nitrogen compounds than that of the non-treated water. The solid phase, namely, the proliferated algae is processed to recover the hydrocarbons produced in the proliferating step. In another embodiment, the cultivated mixture is adjusted to a water content of 60–98% by weight and is then heated at a temperature of 150°–400° C. and a pressure of 16–220 atm. for a period of time sufficient to liberate the hydrocarbon from the microalga and thereby to obtain a hydrocarbon-containing mixture. The hydrocarbon is recovered from the mixture by, for example, solvent extraction. The heating step is preferably performed in the presence of an alkaline substance selected from alkali metal compounds, alkaline earth metal compounds and mixtures thereof.

The hydrocarbon thus recovered can be utilized in the same manner as that of fossil fuel.

The water to be treated in accordance with the method of the present invention is one containing an inorganic nitrogen compound in an amount of generally 0.1 ppm by weight. Such a nitrogen compound-containing water may be, for example, water effluent from sewage treatment plants or facilities in which domestic or factory sewage or foul water is aerobically or anaerobically treated, with or without using microorganisms. Water of lakes, ponds, rivers, etc. may of course be used in the method of the present invention.

The inorganic nitrogen compound may be, for example, a nitrate, nitrite or ammonium salt. The water to be treated generally contains other inorganic compounds such as phosphorus compounds. This is preferable since such compounds serve as nutrients for the microalgae.

Any microalga may be used for the purpose of the present invention as long as it can produce one or more hydrocarbons during the growth thereof. A microalga capable of producing one or more hydrocarbons having at least 17 carbon atoms is preferably used. Such hydrocarbons may be, for example, straight chain hydrocarbons having one or more carbon-carbon double bonds, such as $C_{27}H_{52}$, $C_{29}H_{56}$, $C_{30}H_{50}$, $C_{31}H_{52}$, $C_{32}H_{54}$, $C_{34}H_{58}$ and $C_{36}H_{62}$. Illustrative of suitable microalgae are those belonging to the genus Dunaliella, Spirulina, Euglena, Haematococcus, Porphyridium, Chlamydomonas, Botryococcus, Rivularia, Rhodella and Chlorella. These microalgae are available from, for example, American Type Culture Collection (Rockville, United States of America) and Austin Culture Collection in University of Texas (United States of America).

The cultivation of the microalga in the nitrogen compound-containing water may be performed in any known manner. For the purpose of expediting growth and proliferation of the microalgae, it is preferred that the cultivation be performed at a temperature of 20°–30° C., more preferably about 25° C., in the presence of carbon dioxide while irradiating with light. A carbon dioxide-containing gas discharged as industrial exhaust gas, such as a boiler exhaust gas, may be suitably used. Sunlight is generally used. Electric lamps such as fluorescent lamps may also be used. The cultivation conditions vary with the kind of the microalga used.

It is an object of the present invention to provide a method which can treat an inorganic nitrogen compound-containing water for reducing the concentration of such compounds using a microalga.

Another object of the present invention is to provide a method of the above-mentioned type in which useful hydrocarbons can be produced simultaneous with the treatment of the nitrogen compound-containing water.

It is a further object of the present invention to provide a method of the above-mentioned type which can contribute to the minimization of exhaustion of carbon dioxide to the atmosphere.

It is yet a further object of the present invention to provide a method which permits effective recovery of the hydrocarbons, generally heavy hydrocarbons, from the proliferated microalga.

BRIEF DESCRIPTION OF THE DRAWINGS

Other objects, features and advantages of the present invention will become apparent from the detailed description of the preferred embodiments which follows, when considered in light of the accompanying drawings, in which.

DETAILED DESCRIPTION OF THE PREFERRED EMBODIMENTS OF THE INVENTION

Figure 1:
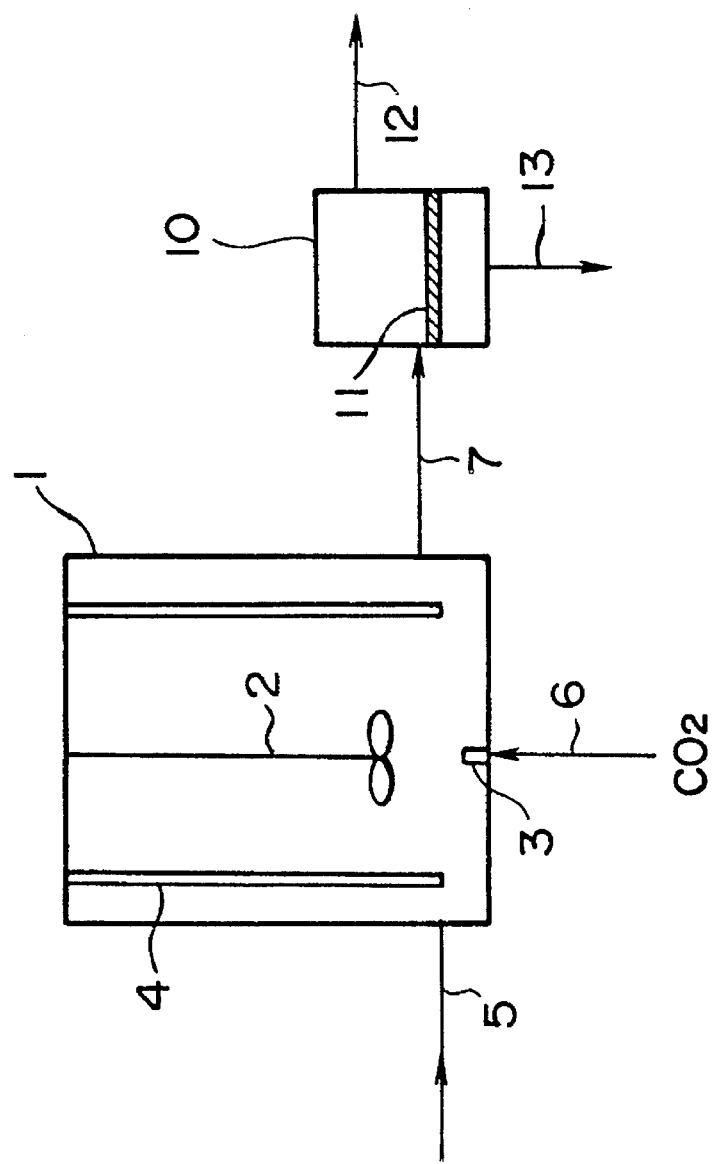
FIG. 1 is a schematic diagram showing an apparatus for carrying out the method of the present invention.

Referring now to FIG. 1, designated as 1 is a bioreactor equipped with a stirrer 2, an aeration nozzle 3 and a plurality of optical fibers 4. The bioreactor 1 contains waste water to be treated which is supplied, continuously or intermittently, thereto through a line 5 and microalga. The microalgae are dispersed in the water with the stirrer 2 and are allowed to grow with irradiation by light supplied through the optical fibers 4 while bubbling carbon dioxide gas supplied through a line 6 and the nozzle 3.

In one embodiment according to the present invention, the alga-containing water is discharged, continuously or intermittently, through a line 7 from the bioreactor 1 and is passed to a solid-liquid separator 10 where the solid phase containing the proliferated alga is separated by, for example filtration with a filter 11. The solid phase (algal paste) is discharged through a line 12 from the separator 10 and is treated for the recovery of hydrocarbons. The liquid phase is discharged through a line 13 and is discarded, recycled to the reactor 1 or fed to a succeeding bioreactor (not shown). The solid-liquid separation may also be effected by sedimentation, centrifugation or in any other suitable manner.

The recovery of hydrocarbons from the microalgae may be performed by, for example, extraction, optionally after drying and destruction, with an organic solvent such as n-hexane.

The apparatus of FIG. 1 is further provided with pumps, valves, motors, a light source, a temperature controller and other parts required to effectively culture and separate the microalgae. However, illustration and explanation of these parts are omitted here.

In another embodiment, the culture containing the purified water and the proliferated microalgae in which the hydrocarbons have been accumulated as the intracellular product is treated for the recovery of the hydrocarbons by a method which includes the steps of:

removing part of the purified water from the culture to obtain a first mixture having a water content of 60–98% by weight, preferably 70–80% by weight, such as by decantation, filtration or the like concentration method;

heating the first mixture at a temperature of 150°–400° C., preferably 200°–300° C., and a pressure of 16–220 atm., preferably 80–130 atm. for a period of time sufficient to liberate the hydrocarbons from the proliferated microalga, generally for 5–180 minutes, thereby to obtain a second mixture containing the liberated hydrocarbons; and recovering the liberated hydrocarbons from the second mixture by, for example, solvent extraction and/or distillation.

It is preferred that, before the heating step, the pH of the first mixture is adjusted to 7–14, more preferably 8–10, for reasons of improved recovery of the hydrocarbons. Thus, before the heating step, 0.1–50%, preferably 1–10% by weight, based on the weight of the proliferated microalga on dry basis, of an alkaline substance such as an alkali metal compound or an alkaline earth metal compound is suitably added to the first mixture. Examples of such alkaline substances include carbonates, acetates, bicarbonates, hydroxides and formates of alkali metals and alkaline earth metals.

By heating the proliferated microalgae under a pressurized condition, the microalgae are lysed to liberate the hydrocarbons accumulated therein as an intracellular product. The pressurization may be by nitrogen gas, air, steam or any available gas.

The following examples will further illustrate the present invention. In the examples, two kinds of thermally sterilized water samples (Sample A and Sample B) discharged from two different domestic sewage purification facilities were treated in accordance with the method of the present invention. *Botryococcus braunii* was used as a microalga. This microalga was incubated in the Chu 13 medium at 25° C. with stirring while bubbling a carbon dioxide gas (1% by volume $CO_2$, 79% by volume $N_2$ and 20% by volume $O_2$) through the medium and irradiating with light using fluorescent lamps at 3,000 lux. After incubation, the microalga was separated by filtration, washed with the water to be treated (Sample A or B) and then used for the treatment of the water to be treated.

EXAMPLE 1

Figure 2:
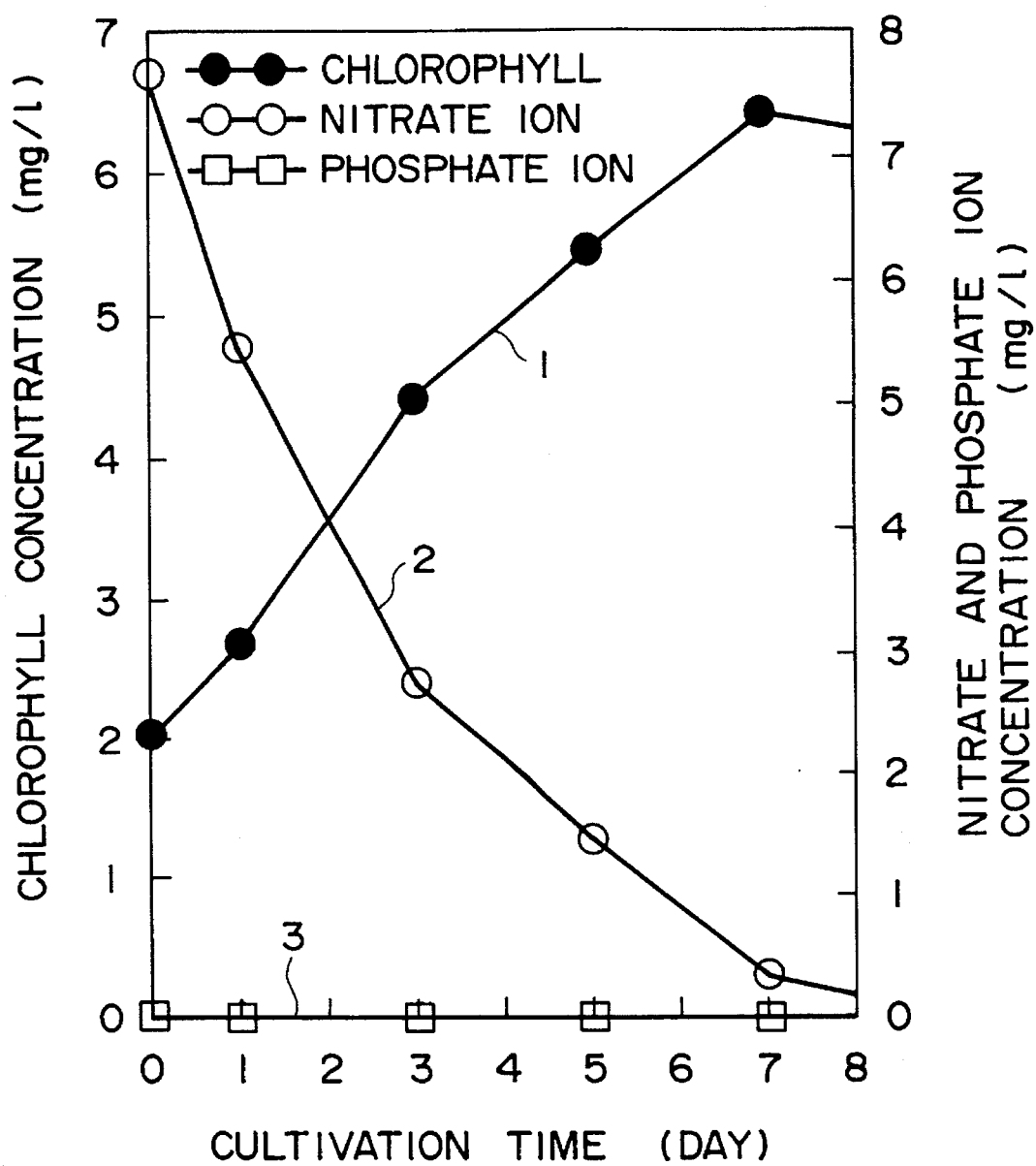
FIGS. 2 and 3 are graphs showing the relationship between the number of cultivation days and the chlorophyll, nitrate ion and phosphate ion concentrations.

The microalga (about 1 g in wet weight) was added into a flask containing 3 liters of sample A and was cultivated at 25° C. with stirring for 9 days while continuously bubbling a carbon dioxide gas and irradiating with light from white fluorescent lamps at 3,000 lux. During the 9 days cultivation, a portion of the culture was occasionally sampled to measure the amount of chlorophyll and the concentrations of nitrate ion and phosphate ion. The nitrate ion concentration was measured by an ion chromatographic method and expressed in terms of the amount (mg) of nitrogen atom per liter of the sample liquid. The phosphate ion was measured by an ammonium molybdate-ascorbic acid method and also expressed in terms of the amount (mg) of phosphorus atom per liter of the sample liquid. The results of the measurement are shown by graph in FIG. 2. The curves 1–3 in FIG. 2 represent the changes of chlorophyll concentration, nitrate ion concentration and phosphate ion concentration, respectively. After 9 days of cultivation, the chlorophyll concentration increased to about 2.8 times that of the initial concentration. The nitrate ion concentration which was initially 7.76 mg/liter was not detected after 9 days cultivation. The phosphate ion concentration which was initially 0.015 mg/liter decreased to less than 0.01 mg/liter after one day from the start of the cultivation. The culture obtained after the 9 days cultivation was filtered and lyophilized to obtain 0.35 g of solids. The solids were ultrasonically extracted with n-hexane to separate 0.186 g (53% by weight) of hydrocarbons.

EXAMPLE 2

Figure 3:
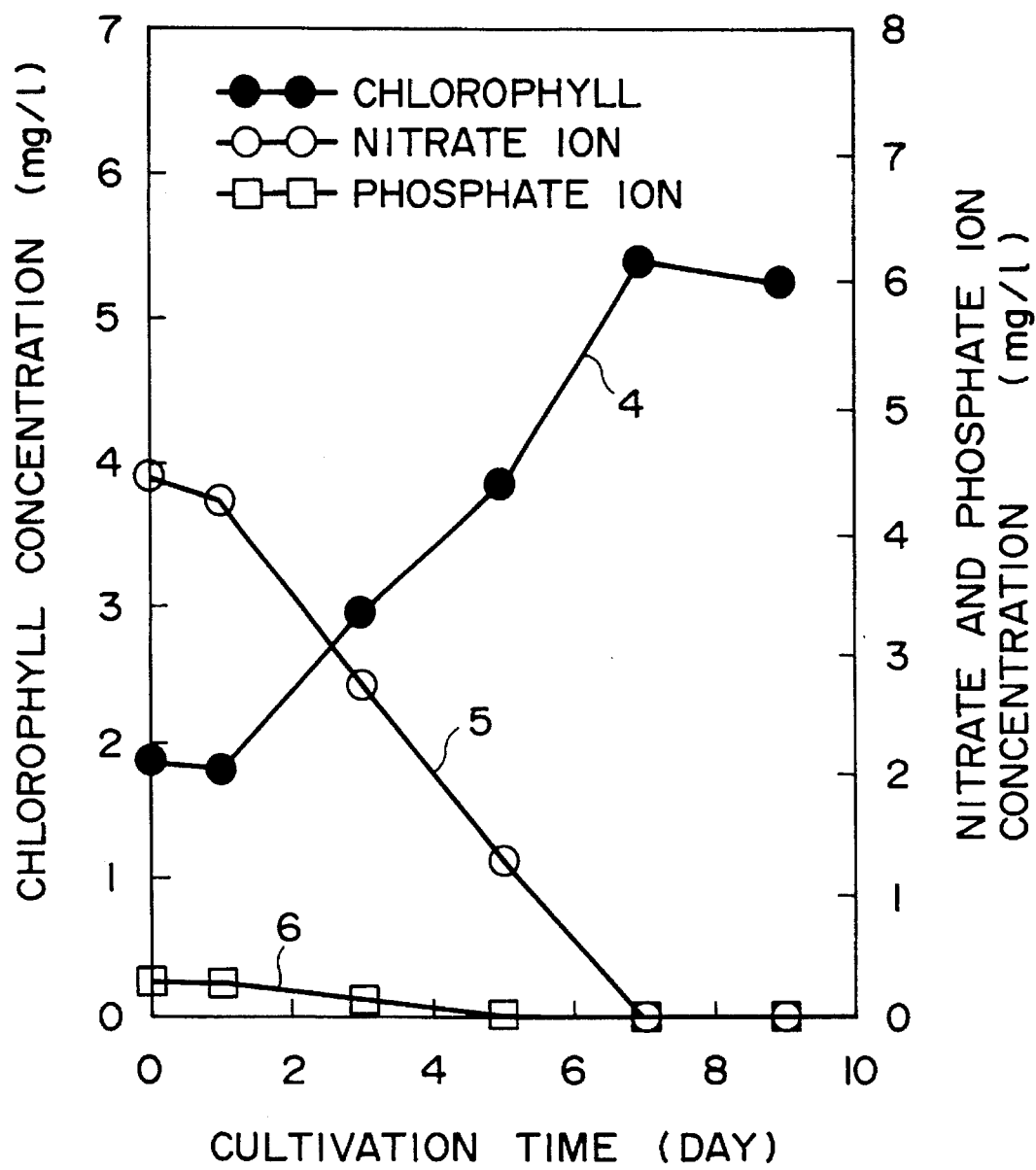

Example 1 was repeated in the same manner as described except that Sample B was substituted for Sample A. The results of the measurement are shown by graph in FIG. 3, in which the curves 4–6 represent the changes of chlorophyll concentration, nitrate ion concentration and phosphate ion concentration, respectively. After 9 days cultivation, the chlorophyll concentration increased to about 2.8 times that of the initial concentration. The nitrate ion concentration which was initially 4.48 mg/liter was not detected after 7 days cultivation. The phosphate ion concentration which was initially 0.29 mg/liter had decreased to less than 0.01 mg/liter after 5 days from the start of the cultivation. The culture obtained after the 9 days cultivation was filtered and lyophilized to obtain 0.34 g of solids. The solids were extracted with n-hexane to separate 0.136 g (40% by weight) of hydrocarbons.

EXAMPLE 3

*Botryococcus braunii* was cultured in the Chu 13 medium at 25° C. with stirring while bubbling a gas containing 1% by volume $CO_2$ through the medium and irradiating with light using fluorescent lamps at 3,000 lux. After incubation, the microalga was separated by filtration, to obtain a first mixture having a water content of 90% by weight. Part of the first mixture (40 g) was placed in an autoclave and pressurized with nitrogen gas (initial pressure: 20 atm.). Then, the autoclave was heated at a rate of 10° C./minute to 300° C., whereby the pressure inside of the autoclave was autogeneously increased to 110 atm. The autoclave was then allowed to stand at 300° C. for 60 minutes. After cooling to room temperature, the resulting second mixture was extracted with dichloromethane. The yield of the hydrocarbon oil (boiling point higher than 40° C.) was found to be 53% by weight (organic matter basis).

EXAMPLE 4

The first mixture obtained in Example 3 was heat-treated in the same manner as described in Example 3 except that 0.15 g of sodium carbonate was added thereto before heating. The yield of the hydrocarbon oil was found to be 64% by weight.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of treating water containing an inorganic nitrogen-containing compound as an impurity, for removal of said nitrogen-containing compound, said method comprising the steps of:

(a) culturing, in the water, a proliferating microalga capable of consuming the nitrogen-containing compound and of producing at least one hydrocarbon as an intracellular product, to consume said nitrogen-containing compound with the simultaneous accumulation of the hydrocarbon in said microalga, thereby to obtain a culture containing the proliferated microalga and purified water;

(b) removing part of the purified water from said culture leaving a first mixture containing said proliferated microalga and 60–98% by weight water;

(c) dissolving in said first mixture 0.1–50%, based on the weight of the proliferated microalga on dry basis, of an alkaline substance selected from the group consisting of alkali metal compounds and alkaline earth metal compounds, to form a second mixture;

(d) heating said second mixture at a temperature of 150°–400° C. and a pressure of 16–220 atm. for a period of time sufficient to liberate the hydrocarbon from the proliferated microalga and to obtain a third mixture containing the liberated hydrocarbon; and (e) recovering the liberated hydrocarbon from said third mixture.

2. A method as claimed in claim 1, wherein said microalga is a member belonging to genus selected from the group consisting of Dunaliella, Spirulina, Euglena, Haematococcus, Porphyridium, Chlamydomonas, Botryococcus, Rivularia, Rhodella and Chlorella.

3. A method as claimed in claim 1, wherein said alkaline substance is at least one compound selected from the group consisting of carbonates, acetates, bicarbonates, hydroxides and formates of an alkali metal and alkaline earth metal.

4. A method as claimed in claim 1, wherein said alkaline substance is incorporated into said first mixture in an amount of 1–10% by weight based on the weight of the proliferated microalga on dry basis.

5. A method as claimed in claim 1, wherein said first mixture has a water content of 70–80% by weight.

6. A method as claimed in claim 1, wherein the pH of said first mixture is adjusted to 7–14 in step (c).

7. A method as claimed in claim 1 wherein the pH of said first mixture is adjusted to 8–10 in step (c).

8. A method as claimed in claim 1 wherein said microalga is a member belonging to a genus selected from the group consisting of Spirulina, Euglena, Haematococcus, Porphyridium, Chlamydomonas, Botryococcus, Rivularia, Rhodella and Chlorella.

9. A method as claimed in claim 1 wherein said microalga is a species belonging to the genus Botryococcus.

10. A method as claimed in claim 1 wherein said microalga is *Botryococcus braunii*.

11. A method as claimed in claim 1 wherein said water is water selected from the group consisting of effluents from sewage treatment plants, aerobically or anaerobically treated factory water, lake water, pond water and river water.

* * * * *